US010088480B2

(12) United States Patent
Boilard et al.

(10) Patent No.: US 10,088,480 B2
(45) Date of Patent: Oct. 2, 2018

(54) METHODS AND COMPOSITIONS FOR ASSESSING SPERMATOZOA IN A SEMEN SAMPLE

(71) Applicants: Mathieu Boilard, Quebec (CA); Lyne Massicotte, Quebec (CA)

(72) Inventors: Mathieu Boilard, Quebec (CA); Lyne Massicotte, Quebec (CA)

(*) Notice: Subject to any disclaimer, the term of this patent is extended or adjusted under 35 U.S.C. 154(b) by 12 days.

(21) Appl. No.: 14/436,652

(22) PCT Filed: Oct. 17, 2013

(86) PCT No.: PCT/CA2013/050788
§ 371 (c)(1),
(2) Date: Apr. 17, 2015

(87) PCT Pub. No.: WO2014/059548
PCT Pub. Date: Apr. 24, 2014

(65) Prior Publication Data
US 2015/0276736 A1    Oct. 1, 2015

Related U.S. Application Data

(60) Provisional application No. 61/715,362, filed on Oct. 18, 2012.

(51) Int. Cl.
*G01N 33/569* (2006.01)
*G01N 15/14* (2006.01)
*G01N 33/50* (2006.01)
*C12N 5/076* (2010.01)
*G01N 15/10* (2006.01)
*G01N 33/487* (2006.01)

(52) U.S. Cl.
CPC ....... *G01N 33/56966* (2013.01); *C12N 5/061* (2013.01); *G01N 15/1459* (2013.01); *G01N 33/48728* (2013.01); *G01N 33/5005* (2013.01); *G01N 33/5091* (2013.01); *G01N 2015/1006* (2013.01); *G01N 2015/1402* (2013.01); *G01N 2015/1488* (2013.01); *G01N 2333/70589* (2013.01)

(58) Field of Classification Search
None
See application file for complete search history.

(56) References Cited

U.S. PATENT DOCUMENTS

| 4,559,309 A * | 12/1985 | Evenson | G01N 21/6428 |
| | | | 250/461.2 |
| 6,342,344 B1 * | 1/2002 | Thomas | C07K 16/28 |
| | | | 435/2 |
| 2004/0244806 A1 * | 12/2004 | Ferree | A61B 17/1671 |
| | | | 128/898 |
| 2011/0270127 A1 * | 11/2011 | Vered | A61B 10/0096 |
| | | | 600/573 |

OTHER PUBLICATIONS http://www.merriam-webster.com/medical/cytometry, accessed May 17, 2016.*
Product list by InvitrogenTM regarding Hoechst stains; Copyright 2005, Molecular Probes, Inc.; 4 pages total. (Year: 2005).*
P.N. Schlegel, Reproduction, Fertility and Development, 2004, 16, 561-572. (Year: 2004).*
Product Information on the LIVE/DEAD® Sperm Viability Kit (L-7011), MP07011, revised Mar. 14, 2001; 3 pages total . (Year: 2001).*
Amaral et al., "Exogenous glucose improves long-standing human sperm motility, viability, and mitochondrial function," *Fertil Steril.*, 96(4):848-50, doi: 10.1016/j.fertnstert.2011.07.1091. Epub Aug. 11, 2011.
Eustache et al., "Evaluation of Flow Cytometric Methods to Measure Human Sperm Concentration," *Journal of Andrology*, 22(4):558-567, 2001.
Hossain, et al., "Flow cytometry for the assessment of animal sperm integrity and funtionality: state of the art," *Asian Journal of Andrology*, 13(3):406-419, 2011, Published online Apr. 11, 2011. doi: 10.1038/aja.2011.15.
Mahfouz, et al., "The diagnostic and therapeutic applications of flow cytometry in male fertility," *Archives of Medical Science*, 5(IA):S99-S108, 2009.
Martinez-Pastor, et al., "Probes and Techniques for Sperm Evaluation by Flow Cytometry," *Reprod Dom Anim*, 45(Suppl. 2):67-78, 2010.

* cited by examiner

*Primary Examiner* — Christina M Borgeest
(74) *Attorney, Agent, or Firm* — Klarquist Sparkman, LLP

(57) ABSTRACT

The present invention relates to the field of mammalian reproduction and provides methods, compositions and kits for detecting and assessing spermatozoa and intervening cells in a semen sample which are applicable to human and veterinary uses. Various aspects of the present invention provide for a cytometric multiparametric approach for determining spermatozoa concentration in a semen sample, wherein the cytometric multiparametric approach involves use of one or more spermatozoa-specific detection agents for detection of spermatozoa in the semen sample and one or more intervening cells-specific detection agents.

15 Claims, 4 Drawing Sheets

| Lasers | Blue (488) | | | | | | U.V. (355nm) | |
|---|---|---|---|---|---|---|---|---|
| PMT | A | B | C | D | E | F | A | B |
| LP | 685 | 635 | 600 | 550 | 505 | | 505 | |
| BP | 695/40 | 670/30 | 610/20 | 575/26 | 530/30 | 488/10 | 530/30 | 450/50 |

METHODS AND COMPOSITIONS FOR ASSESSING SPERMATOZOA IN A SEMEN SAMPLE

PRIORITY INFORMATION

This is the U.S. National Phase of PCT/CA2013/050788, filed on Oct. 17, 2013 and published in English, which claim the benefit of U.S. Provisional Application No. 61/715,362 filed on Oct. 18, 2012, entitled "METHOD AND COMPOSITION FOR SIMULTANEOUS DETERMINATION OF LEUKOCYTE AND SPERMATOZOA CONCENTRATION OF AN EJACULATE". U.S. Provisional Application No. 61/715,362 is incorporated herein by reference in its entirety.

TECHNOLOGICAL FIELD

The present invention relates to the field of mammalian reproduction and provides methods, compositions and kits for detecting and assessing spermatozoa and intervening cells in a semen sample which are applicable to human and veterinary uses.

BACKGROUND INFORMATION

To this date, the evaluation of the success or the failure of vasectomy as well as the detection of problems associated with male fertility have been established by performing analyses such as post-vasectomy spermograms or fertility spermograms.

Such analyses typically involve the step of collecting a semen sample from the subject under examination and rapidly analysing the sample (within about 2 hours for vasectomy cases and within about 1 hour for fertility cases).

For current post-vasectomy spermograms a sample of the ejaculate is applied onto a microscope slide or to a hemocytometer for the determination of spermatozoa concentration by microscopic observation. The success of vasectomy is confirmed if a concentration of less than $0.1 \times 10^6$ spermatozoa/mL is observed.

Proof or demonstration of the absence of spermatozoa in a semen sample obtained post-vasectomy may be more complex as an absence of spermatozoa on the microscope slide or on the hemocytometer may be the consequence of actions such as pipetting, loading or miss-observation rather than a direct consequence of the vasectomy procedure.

The reference values confirming the success of a vasectomy are set as $<0.1 \times 10^6$ spermatozoa/mL by the American Urological Association (AUA) recommendations or as $<10 \times 10^3$ spermatozoa/mL by the European Association of Urology (EAU). It is thus practically impossible to evaluate enough of the sample by microscopy to obtain a decent reproducible value. Visualisation of the entire hemocytometer represents examination of a 0.1 μL sample. For this sample volume, the reference value represents the observation of no more than 10 spermatozoa if the AUA recommendations are followed or of a single spermatozoon if the EAU recommendations are followed, giving rise to variations equal to 10% to 100% of the reference values each time a single cell is observed.

According to the World Health Organization (WHO) (World Health Organization (2010): *WHO Laboratory Manual for the Examination and Processing of Human Semen*, Fifth edition), the concentration of leukocytes in an ejaculate is to be determined by spermogram analysis. Leukocytes present in the ejaculate can create an oxidative stress that can be detrimental to spermatozoa ability to fertilize or can be an indicator of infection. The ability of the spermatozoa to fertilize as well as the presence of an infection are thus important factors to monitor by spermogram following procedures such as vasectomy and vasovasostomy. They are also important parameters in situations where conception is awaited since the presence of leukocytes is associated with production of reactive oxygen species (ROS) in the ejaculate. High ROS concentrations are well known to be detrimental to sperm function.

Determining leukocyte concentration in a semen sample is also problematic because the normal reference values are below 1 million cells per mL (1 M/mL). Consequently, concentrations are based on very few cells. In addition, leukocytes can easily be confounded with immature germ cells due to their similar shape and size.

The WHO suggests a method of microscopic immunofluorescence to confirm the identity of leukocytes in a semen sample. Although this protocol allows for the distinction of leukocytes from other cell types, it is laborious and presents standardization difficulties. Moreover, this protocol does not allow for cell concentration measurements. Even if it could allow for such measurements, the number of cells examined by using such a protocol would still remain very low and would give rise to unacceptable variations in the test results.

Although sperm concentration is a key element of the actual post-vasectomy spermograms, such spermograms are not controlled for the ability to determine sperm concentration in a post-vasectomy sample. The only controls actually available address the ability to confirm the presence or absence of spermatozoa but not spermatozoa concentration.

Both the AUA and the EAU mention that although sperm concentration is a key point, sperm motility is also important. No motile spermatozoa should be observed following a vasectomy no matter what the concentration is. This may however be problematic in that there is a possibility that spermatozoa motility has faded out by the time the semen sample reaches the laboratory for analysis.

There is thus a need in the field of fertility for new and more accurate, quantitative, manageable, controllable and valid methods to evaluate the success of vasectomy and to determine the concentration of spermatozoa in semen samples as well as to assess the integrity, function, activity and motility of spermatozoa in semen samples.

SUMMARY OF THE EMBODIMENTS OF THE INVENTION

Various aspects of the present invention may provide for a method for determining the amount of spermatozoa in a semen sample, the method comprising: a) distinguishing a population of spermatozoa in the semen sample from a population of intervening cells in the semen sample using cytometry; and b) determining the amount of spermatozoa in the population of spermatozoa of a) using cytometry; wherein the amount of spermatozoa determined in b) is indicative of the amount of spermatozoa in the semen sample.

Various aspects of the present invention may provide for a method for determining the amount of spermatozoa and the amount of intervening cells in a semen sample, the method comprising: a) distinguishing a population of spermatozoa in the semen sample from a population of intervening cells in the semen sample using cytometry; b) determining the amount of spermatozoa in the population of spermatozoa of a) using cytometry; and c) determining the amount of intervening cells in the population of intervening cells of a) using cytometry; wherein the amount of spermatozoa determined in b) is indicative of the amount of spermatozoa in the semen sample; and wherein the amount of intervening cells determined in c) is indicative of the amount of intervening cells in the semen sample.

Various aspects of the present invention may provide for a method for detecting viable spermatozoa in a semen sample, the method comprising: a) distinguishing a population of spermatozoa in the semen sample from populations of intervening cells in the semen sample using cytometry; and b) identifying viable spermatozoa in the population of spermatozoa of a) using cytometry; wherein identification of viable spermatozoa in b) is indicative of viable spermatozoa in the semen sample.

Various aspects of the present invention may provide for a method for detecting viable spermatozoa in a semen sample, the method comprising: a) distinguishing a population of spermatozoa in the semen sample from a population of intervening cells in the semen sample using cytometry; and b) confirming acrosome integrity of the spermatozoa of a) using cytometry; wherein confirmation of acrosome integrity in b) is indicative of viable spermatozoa in the semen sample.

Various aspects of the present invention may provide for a method for assessing recovery of a male subject following surgical intervention to the subject's reproductive apparatus, the method comprising: a) measuring the amount of leukocytes in a first semen sample from the subject using cytometry obtained at a first time; b) measuring the amount of leukocytes in a further semen sample from the subject using cytometry obtained at a further time; wherein the amount of leukocytes in the further semen sample being lower than the amount of leukocyte in the first semen sample is indicative of recovery.

Various aspects of the present invention may provide for the use of anti-CD45 antibodies for detection and/or quantification of leukocytes in a semen sample; wherein the detection and/or quantification is performed by flow cytometry.

Various aspects of the present invention may provide for the use of a cytometric multiparametric approach for determining spermatozoa concentration in a semen sample, wherein the cytometric multiparametric approach involves use of one or more spermatozoa-specific detection agents for detection of spermatozoa in the semen sample and one or more leukocyte-specific detection agents for detection of leukocytes in the semen sample.

Various aspects of the present invention may provide for the use of a cytometric multiparametric approach for determining spermatozoa concentration in a semen sample, wherein the cytometric multiparametric approach involves use of one or more spermatozoa-specific detection agents for detection of spermatozoa in the semen sample, one or more leukocyte-specific detection agents for detection of leukocytes in the semen sample and one or more epithelial cell-specific detection agents for detection of epithelial cells in the semen sample.

Various aspects of the present invention may provide for the use of a cytometric multiparametric approach for assessing spermatozoa viability and/or function in a semen sample, wherein the cytometric multiparametric approach involves use of one or more viability dyes, one or more an acrosomal integrity detection agents and one or more leukocyte-specific detection agents.

Various aspects of the present invention may provide for a kit for conservation of a semen sample comprising a collector tube for collection of the semen sample and one or more containers containing one or more reagents for analysis of the semen sample and one or more containers containing one or more reagents for conservation of the semen sample together with instruction for conservation of the semen sample.

DETAILED DESCRIPTION OF THE EMBODIMENTS

Figures 1, 2:
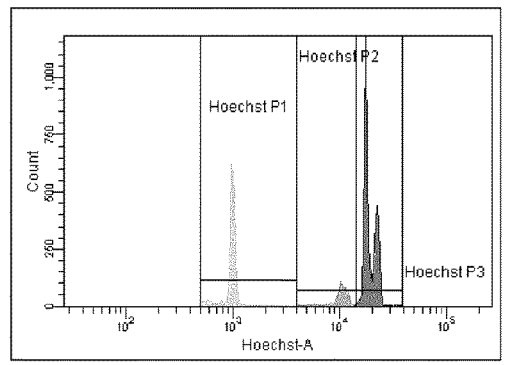
FIG. 1 is a graph illustrating a configuration of the BD LSR Fortessa.
FIG. 2 illustrates a frequency histogram of the Hoechst emission showing analysis gates 1, 2 and 3.

As used herein, the expression "semen sample" or "sperm sample" refers to any material containing sperm, whether processed or unprocessed, and includes ejaculates, electroejaculates, sperm isolated from testes or epididymes extended semen, sperm prepared by swim-up procedures, and sperm prepared by percoll gradient centrifugation.

The present invention finds uses in the analysis of semen samples from a variety of species (e.g., humans, bovines, primates, sheep, pigs, horses, rodents, camels, goats, bison, buffalo, llamas, foxes and ferrets). Furthermore, the samples may be collected by a variety of methods. In some embodiments of the present invention, the semen sample is from an ejaculate. In other embodiments, the semen sample is obtained by electroejaculation. In still other embodiments, the semen sample is obtained surgically from the epididymis or the testies. In some embodiments, the semen sample is analyzed without further processing except for preparation for flow cytometry, immunocytochemistry, or ELISA. However, in other embodiments, the sperm may be subjected to various preparation procedures known in the art (e.g., sperm swim-up or percoll gradient centrifugation).

As used herein, the term "measuring" refers to the act of determining the dimensions, quantity, or capacity of a material.

As used herein the term "antibody" refers to a glycoprotein evoked in an animal by an immunogen (antigen). An antibody demonstrates specificity to the antigen, or, more specifically, to one or more epitopes contained in the immunogen. Native antibody comprises at least two light polypeptide chains and at least two.heavy polypeptide chains, including, but not limited to IgG, IgM, IgA, IgE, and IgD. Each of the heavy and light polypeptide chains contains at the amino terminal portion of the polypeptide chain a variable region (i.e., $V_H$ and $V_L$ respectively), which, contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "$C_L$ region" and the constant region of the heavy chain is referred to as the "$C_H$ region".

As used herein, the term "fertility" refers to the ability to conceive and the term "infertility" refers to the inability to conceive.

As used herein, the expression "flow cytometry" refers to an assay in which the proportion of a material (e.g., spermatozoa) in a sample is determined by labelling the material (e.g., by binding a labelled antibody to the material).

As used herein, the term "quantitating" refers to the act of determining the amount or proportion of a substance (e.g., sperm) in a sample.

As used herein, the term "acrosome" refers to an organelle that develops over the anterior half of the head in the spermatozoa of many animals. It is a cap-like structure derived from the Golgi apparatus.

As used herein, the expression "acrosome reaction" or "acrosomal reaction" refers to a reaction which a sperm undergoes naturally during the process leading up to fertilization. The reaction, which requires the activation of complex signaling events involving calcium ion, sodium ion, potassium ion, chloride ion, bicarbonate, cyclic amp, cellular membrane potential variations and protein phosphorylation inside the spermatozoa is a morphological event in which the plasma membrane and the outer acrosomal membrane of the spermatozoan undergo a multipoint fusion (Green, D. P. L., In: Johnson, M. H., ed., Development in Mammals, North Holland, Amsterdam, 1978, Vol. 3, pp. 65-81)). This fusion, which is considered similar to the fusion of lysosomal membranes with a cell's plasma membrane, similarly leads to the release of hydrolytic enzymes contained within the acrosome (Akruk, S. R. et al., Gamete Res. 2:1-3 (1979). Among the released enzymes is acrosin. It is thought that elevation of calcium ions in the cytoplasm between the plasma and outer acrosomal membranes is the key event preceding the acrosome reactions. In the natural process, sperm undergo this reaction upon contact with the zona pellucida, which is an acellular glycoprotein layer surrounding the oocyte. The hydrolytic enzymes permit penetration of the sperm through the zona pellucida to reach the oocyte membrane, where fusion occurs.

A number of techniques are known in the art for inducing an acrosome reaction under in vitro conditions (see, for example, Tomkins, P. T., International Patent Publication WO 89/02743 (1989)). These sperm treatment methods include, but are not limited to: (1) preincubation in simple or complex culture media supplemented with albumin or serum (Miyamoto, H. et al., J. Reprod. Fert. 32:193-205 (1973)); (2) exposure to high ionic strength media (Brackett, B. G. et al., Biol. Reprod. 12:260-274 (1972); (3) treatment with a calcium ionophore, such as A23187 (Aitken, R. J. et al. J. Androl. 56:321-329 (1984)); (4) direct microinjection of sperm (Lassalle, B. et al., Gamete Res. 16:69-78 (1987)); (5) exposure to phosphatidyl choline liposomes (Graham, J. K. et al., Biol. Reprod. 35:413-424 (1986)); (6) preincubation in simple medium supplemented with defined synthetic polymers and high calcium (Tompkins, P. T. et al., Hum. Reprod. 3:367-376 (1988)); (7) preincubation in the presence of glycosaminoglycans (Lee, C. N. et al., J. Anim. Sci. 63:861-867 (1986)); (8) preincubation for 48 hours at 4.degree. C. in TEST-yolk buffer (Bolanos, J. R., Fertil. Steril. 39:536-540 (1983)); (9) electropermeabilization or electroporation by application of an electric field sufficient to raise the spermatozoal plasma membrane potential from about −70 mV to +1 V to allow an influx of calcium ions (Tompkins, P. T., 1989, supra); (10) addition of follicular fluid (Suarez, S. S. et al., Gamete Res. 14:107-121 (1986) and/or zona pellucida extract to a sperm suspension. These sperm treatment methods may further include, stimulation with thapsigargin, stimulation with progesterone stimulation and exposition to ZP3.

As used herein the term "leukocyte" refers to cells of the immune system involved in defending the body against both infectious disease and foreign materials. Five different and diverse types of leukocytes exist, but they are all produced and derived from a multipotent cell in the bone marrow known as a hematopoietic stem cell. They live for about three to four days in the average human body.

Unless defined otherwise, all technical and scientific terms used herein have the same meaning as commonly understood by one of skill in the art to which the invention pertains.

Several studies have used flow cytometry in order to determine spermatozoa concentration in a sample comprising spermatozoa such as, for example, a semen sample. The common problem with current techniques for determining spermatozoa concentration in a semen sample using flow cytometry is that the identification of the events corresponding to the presence of spermatozoa is very weak. Most of the known cytometry analyses that are aimed at the identification of spermatozoa are based on a combination of shade/light diffracting properties (e.g., forward/side scatter).

Typically, cells are analyzed and sorted on a flow sorter based on the properties of the cells to scatter light forward and to the side. In each experiment parameters are empirically established regarding the forward and side scatter properties. In general, the gain on the photomultiplier tubes detecting the forward-scattered light and the side-scattered light in each dimension is adjusted to distribute the array of signals from the cells across the channels available for analysis in a manner well known to one skilled in the art. Under these circumstances a characteristic pattern, or scattergram, is observed. Further analysis may be carried out by staining the cells with fluorescent-coupled antibodies or by subjecting the cells to hybridization with fluorescent-coupled probes. Under these conditions cells that have particular light scattering properties are also analyzed for the presence of fluorescence.

However, semen samples as well as solution media for cytometry may comprise debris that can mimic the light scattering signature of spermatozoa and can skew the analysis; especially when so few spermatozoa are present in a sample such as for example in a post-vasectomy sample to be subjected to a spermogram or in the case of oligozoospermic semen samples to be submitted for fertility evaluation. Seminal plasma comprises leukocytes and epithelial cells. If not identified properly, some leukocytes and and some epithelial cells can be counted as spermatozoa and can skew the analysis.

In some embodiments, the present invention relates to methods for the determination of the concentration of spermatozoa in a semen sample and the proportion of live spermatozoa therein. Such methods comprise subjecting the semen sample or a diluted subsample of the semen sample to selective staining of live and dead spermatozoa and determining the total concentration of the spermatozoa and the proportion of live spermatozoa by a detection means responsive to the selective staining.

One way of determining the total concentration of spermatozoa and the proportion of live spermatozoa is by use of flow cytometry where the detection means is a photo detector and where information relating to the concentration is obtained by incorporation of an internal standard in the form of fluorescent particles, but other determination methods based on selective staining have been developed during recent years and may also be adaptable to the methods of the present invention.

The data derived from the cytometry analysis may be used for routine evaluation of semen, e.g. for artificial insemination and for determination of the degree of dilution required for securing an adequate number of live sperm cells in each insemination dose.

An important aspect of the methods of the invention is performed using a flow cytometer, such as a laser scanning cytometer. In this case, the determination of the concentration parameter is obtained by combining the sample with an internal concentration standard means determining the total concentration of the spermatozoa. The internal concentration standard means may be any concentration standard means that can be suitably combined with the sample and detected by the detection means to function as a reference indicative of the concentration of the spermatozoa. The internal concentration standard means may suitably be constituted by standardization particles, the standardization particles being added in a predetermined number per weight or normally volume amount of the sample or subsample. The standardization particles are fluorescent particles, in particular fluorescent beads.

The size and total spermatozoa concentration of the sample may suitably be adapted so that the number of spermatozoa corresponds to between one tenth and ten times the number of standardization particles, in particular to between one quarter and four times the number of standardization particles, such as to between half and twice the number of standardization particles.

The beads may be provided in a suspension comprising beads and diluent. It is an advantage of a suspension comprising both the beads and the diluent that the suspension may be manufactured by a manufacturer in a highly automated process to obtain a very accurate number of beads in the suspension. Furthermore, the suspension comprising the diluent and the beads may be manufactured in tubes, the tubes being suitable as measuring chambers in fluorescent activated cell sorters, such as flow cytometers. Thereby, inaccuracies originating from redistribution and dilution of the suspension are minimized. Still further, using tubes from the same manufacturing process with the same lot number, corresponding results may be obtainable independently of different apparatuses being used by different users.

The diluent may be a diluent which is non-toxic to sperm and which sustains viability during the staining and analysis procedures. The diluent may be a diluent decreasing the staining time. The diluent may comprise any medium capable of preventing spermatozoa from sticking to the side walls of the measuring chamber or measuring tube, such as a chemical compound, such as a protein, such as BSA, or another suitable compound such as polyvinyl alcohol (PVA), etc.

Examples of dyes useful for staining the live spermatozoa include, but are not limited to SYBR-14 and MPR71292, and examples of dyes for staining dead or dying spermatozoa include but are not limited to ethidium-homodimer-2.

Various aspects of the present invention also relate to methods that allow for more specific and more accurate detection of spermatozoa as well as detection of intervening cells in a semen sample and relate to methods for better and more accurate assessment of spermatozoa viability and motility in a semen sample from normal male subjects as well as from vasectomised male subjects.

In some implementations, the methods defined herein use a multiparametric approach to detect the present of spermatozoa in a semen sample and/or to determine the concentration of spermatozoa in a semen sample as well as to detect the present of intervening cells in the semen sample and to determine the concentration of intervening cells in the semen sample. As used herein, the expression "intervening cells" refers to non-spermatozoa cells, such as for example, leukocytes, epithelial cells, monocytes, eosinophils, neutrophils, T-cells, B-cells, platelets, red-blood cells, mast cells, dendritic cells, NK cells, macrophages or any combinations thereof.

In some other implementations, the methods defined herein use a multiparametric approach to detect and/or assess the motility, function and/or the activity of spermatozoa in a semen sample and to assess the function or the activity of intervening cells in the same sample.

Such multiparametric approach involves the use of a cell sorter apparatus such as a cytometer, in particular a flow cytometer, that allows cell identification, cell gating and cell enumeration and/or involves a combination of spermatozoa enumeration by flow cytometry, rare cell detection and intervening cells detection (see e.g., McCoy, Flow Cytometry and Clinical Diagnosis, Karen et al., eds., ASCP Press, Chicago, p. 26-55 [1994]; Flow Cytometry: A Practical Approach, Ormerod, ed., IRL Press, Oxford [1994]).

In other aspects, the present invention relates to a flow cytometry analysis for detection of spermatozoa among intervening cells in a semen sample in order to determine spermatozoa concentration and/or to determine the concentration of intervening cells.

In some implementations of these aspects, the intervening cells are leukocytes.

In other implementations of these aspects, the intervening cells are epithelial cells.

Detection of spermatozoa within a semen sample by cytometry analysis may be achieved using agents such as, but not limited to, spermatozoa-specific detection agents.

Detection of leukocytes within a semen sample by cytometry analysis may be achieved using agents such as, but not limited to, leukocytes-specific detection agents.

Detection of epithelial cells within a semen sample by cytometry analysis may be achieved using agents such as, but not limited to, epithelial cell-specific detection agents, such as but not limited to antibodies against CD104, which antibodies are coupled to a fluorochrome. Antibodies against other epithelial cell markers may be useful in the methods of the present invention such as for example, antibodies against CD 118, CD138, CD296, CD324, CD326, CD331, CD332, CD334 as well as antibodies against other markers of epithelial cells.

Examples of spermatozoa-specific detection agents include, but are not limited to, DNA dyes. Examples of DNA dyes include, but are not limited to, Hoechst, DAPI, propidium iodide, SYBR 14 dye, or any other DNA dyes that are known in the art.

Leukocytes-specific detection agents include, but not limited to, fluorescent inhibitors specific for leukocytes, fluorescent antibodies that specifically recognise leukocytes, or other chemicals or biotechnological detection methods directed against leukocyte-specific proteins or leukocytes-specific lipids or any another types of molecules that are specific to leukocytes. For example, detection of leukocytes may be accomplished using antibodies against CD45 (anti-CD45 antibodies). Antibodies against CD44, CD47, CD47R, CD50, CD53, CD54, CD55, CD58, CD59 and antibodies against other known markers by leukocytes may also be useful in the methods of the present invention.

Spermatozoa and intervening cells in a semen sample may be enumerated using for example, beads that are added to the sample or using labels that are specific or rendered specific to spermatozoa or the intervening cells through known techniques in the art.

In some embodiments, the methods defined herein comprise the use of cell viability dyes for assessment of the viability of spermatozoa in a semen sample.

In some implementations of these embodiments, the methods comprise the use of cell viability dyes in combination with a leukocyte-specific detection agent for cytometry analysis.

Viability dyes useful for detection and/or quantification of functional spermatozoa and for detection and/or assessment of spermatozoa function and/or activity include, but are not limited to, acetoxy-methyl ester dye, mitochondrial function dye, other organelle dye, fixable viability dye. Examples of viability dyes include but are not limited to Fixable Viability Dye eFluor® 455UV, Fixable Viability Dye eFluor® 450, Fixable Viability Dye eFluor® 506, Fixable Viability Dye eFluor® 520, Fixable Viability Dye eFluor® 660, Fixable Viability Dye eFluor® 780, Calcein AM, Calcein Violet AM, Calcein Blue AM, Propidium Iodide, and Sybr dyes including Sybr 14, Syto dyes and 7-AAD.

In a further embodiment, the present invention comprises the use of indo-1, BCECF or Snarf-1 or any other acetoxy-methylester dyes as viability dyes.

These dyes may be used in combination with a fluorescent inhibitor, fluorescent antibody or other chemical or biotechnological detection methods directed against a protein or a lipid or another type of molecule specific for leukocytes.

Such detection step may be followed by characterization and quantification of the spermatozoa and/or the leukocytes also by flow cytometry. Additional antibodies that may be used for further characterization of the leukocytes into lymphocytes (e.g., anti-CD49d antibodies, anti-CD218b antibodies, anti-CD290 antibodies, anti-CD312 antibodies), NK cells (e.g., anti-CD56 antibodies, anti-CD57 antibodies, anti-CD161 antibodies, anti-CD48 antibodies, anti-CD159 antibodies), monocytes (e.g., anti-CD14 antibodies, anti-CD11 b antibodies), eosinophils (e.g., anti-CD44 antibodies), neutrophils (e.g., anti-CD15 antibodies, anti-CD16 antibodies), etc.

In a further embodiment, the present invention comprises the detection and the determination of the concentration of epithelial cells in a semen sample by a fluorescent inhibitor, fluorescent, antibody or another chemical or biotechnological detection method directed against a protein or a lipid or another type of molecule particular to epithelial cells known in the art, which may be used alone or in combination with a fluorescent inhibitor, fluorescent, antibody or another chemical or biotechnological detection method directed against a protein or a lipid or another type of molecule specific to leukocytes for detection and determination of the concentration of leukocytes in the semen sample.

The methods defined herein may further comprise the steps of measuring spermatozoa intracellular parameters such as, but not limited to, calcium concentration, ion concentration, pH or other parameters according to methods and techniques known in the art.

According to other embodiments, the present invention relates to methods for the measurement of spermatozoa viability, acrosome reaction and intervening cells concentration in a semen sample by a single multiparametric approach including the use of cytometry.

In some implementations of this embodiment, detection of acrosomal integrity is performed using acrosomal integrity detection agent such as labels that monitor acrosomal change, such as for example, but not limited to, anti-CD46 antibodies or Fluorescein isothiocyanate-PNA (PNA-FITC), in combination with a cell viability dye and leukocyte-specific antibody or a fluorescent leukocyte-specific inhibitor, leukocyte-specific antibody or another chemical or biotechnological detection methods specific for detection of leukocytes, such as but not limited to, an anti-CD45 antibody. In such implementations, anti-CD46 antibodies or PNA-FITC may be replaced by other agglutinin coupled to FITC or by PNA coupled to other fluorochromes.

Other viability dyes may be used for example, Dapi can be replaced by an acetoxy methyl ester dye that is amphiphylic and is trapped inside living cell by the action of endogenous esterases like Indo-1 AM, SBFI, PBFI, MQAE or others. This allows for simultaneous intracellular measurements in spermatozoa like calcium (indo-1 am) or intracellular pH (BCECF-am or carboxy Snarf-1).

In a further embodiment, the methods of the present invention comprise steps for stimulating capacitation and/or acrosome reaction with techniques and agents as defined herein prior to determining spermatozoa concentration and function.

In a further embodiment, the present invention relates to a kit for extended conservation of a semen sample prior to analyses.

In some implementations of this embodiment, the kit comprises a collector tube for collection of the semen sample.

In some other implementations of this embodiment, the kit comprises a collection tube as well as one or more other containers containing one or more reagents for analysis of the semen sample. Such reagents may include reagents for labelling and/or staining spermatozoa in the sample and/or the intervening cells in the sample such as leukocytes and/or epithelial cells as well as reagents useful in for detection of acrosome and/or assessment of spermatozoa viability and/or function.

In some other implementations of this embodiment, the one or more reagents include stabilizing or fixating agents such as for example, but not limited to, formaldehyde as well as other reagents for storage, conservation and/or transport of the semen sample.

In some implementations of this embodiment, the kit allows the user to collect a semen sample in the collection tube and then to mix the collected semen with one or more of the reagents.

The kits of the present invention may further comprise instructions on how to use the kit.

EXAMPLES

Example 1

A semen sample from a vasectomised male was collected into a pre-weighted container sterile collection tube. The total semen sample volume was determined by weighing the sample-containing tube and by subtracting the empty volume weight from the result. This difference corresponding to semen weight was multiplied by semen density (1.07 g/ml) to obtain semen volume (ml). Semen density typically varies from about 1.04 g/mL to about 1.11 g/mL and is preferably about 1.07 g/mL. Typical volume varies between about 1.5 mL to about 8 mL, preferably between about 1.5 and about 5 mL.

The pH of the sample was measured. Reference values for pH stand between about 7.0 to about 8.3. The pH of the semen sample may be measured using for example, pH paper strips.

Subsequent to liquefaction which was carried out for a duration of about 30 minutes, 100 µl of semen was transferred to a cytometry tube (BD Falcon™ 352052) containing 845 µl of Phosphate Buffered Saline (PBS: 137 mM NaCl, 2.7 mM KCl, 10 mM $Na_2HPO_4$, 1.47 mM $KH_2PO_4$), 5 µl of 720 µM Hoechst 33342 (Molecular probes H1399) for DNA quantification, 5 µl of PerCp-conjugated anti-human CD45 (BioLegend 304026) antibody for leukocyte double identification, and 2 µl of 10 nM 3,3'-dihexyloxacarbocyanine iodide (DiOC6) for living cells quantification (Molecular Probes D273). The sample is then incubated at 37° C. for a period of 15 minutes in the dark to avoid fluorochrome bleaching. After the incubation is completed, 43 µl of beads suspension (Bangs Laboratories #580) are added to the tube.

Example 2

The tube as defined in EXAMPLE 1 was incubated for 15 minutes at 37° C. prior to addition of 50 000 fluorescent beads for internal photomultiplier control and cell enumeration.

A BD LSR Fortessa cytomer equipped with a UV (350 nm) laser and a blue (488 nm) laser was used. FIG. 1 indicates the cytometer configuration.

A first gating step was performed to identify the first, second and third peak of hoechst corresponding to beads, spermatozoa and leukocytes on a frequency histogram. Each peak was gated. These correspond to gates 1, 2 and 3 respectively as shown on FIG. 2.

Figure 3:
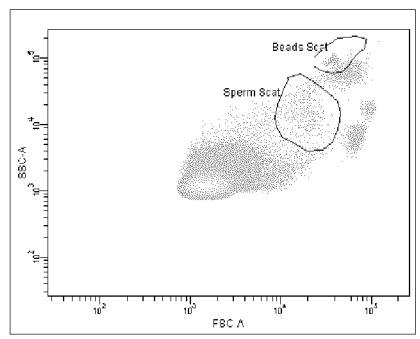
FIG. 3 illustrates a side-scatter vs forward scatter density plot of all events showing analysis gates 4 and 5.

Second, spermatozoa and beads were gated on a side scatter vs. forward scatter density plot. These are gates 4 and 5 as shown in FIG. 3.

Then, bead gates were intersected (1 and 5) to create a new gate (6) so that events that are in both the hoechst gate corresponding to beads (1) and the scatter gate corresponding to beads (5) were considered as beads.

Spermatozoa gates were intersected (2 and 4) to create another new gate (7) so that events that are in both the hoechst gate corresponding to spermatozoa (2) and the scatter gate corresponding to spermatozoa (4) were considered as spermatozoa.

Figure 4:
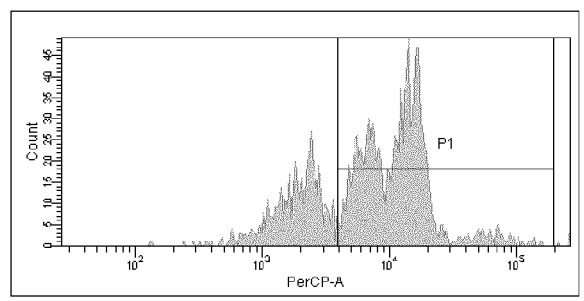
FIG. 4 illustrates a frequency histogram of the PerCp emission showing analysis gate 9.

Then another gate (8) was created by displaying gate 3 events on a CD45 plot and by selecting CD45+ cells. FIG. 4 is illustrative of this step.

A final gate was created by displaying gate 7 events on a plot showing the intensity of the viability dye and by selecting the population of functional cells.

Figure 5:
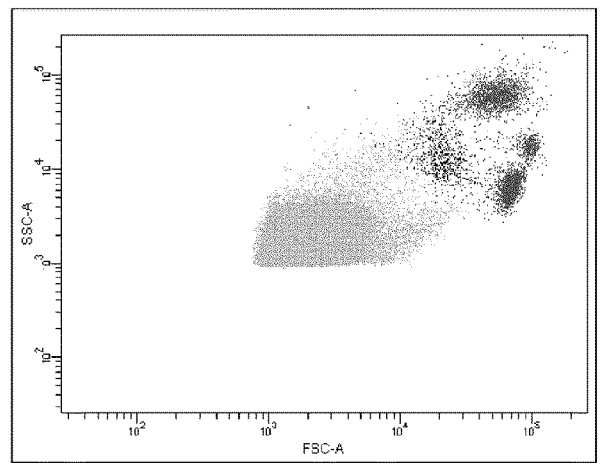
FIG. 5 illustrates a side-scatter vs forward scatter dot plot of all events showing properly identified debris (grey), beads (yellow), spermatozoa (black) and leukocytes (red).

The final results are shown on FIG. 5.

Figure 6:
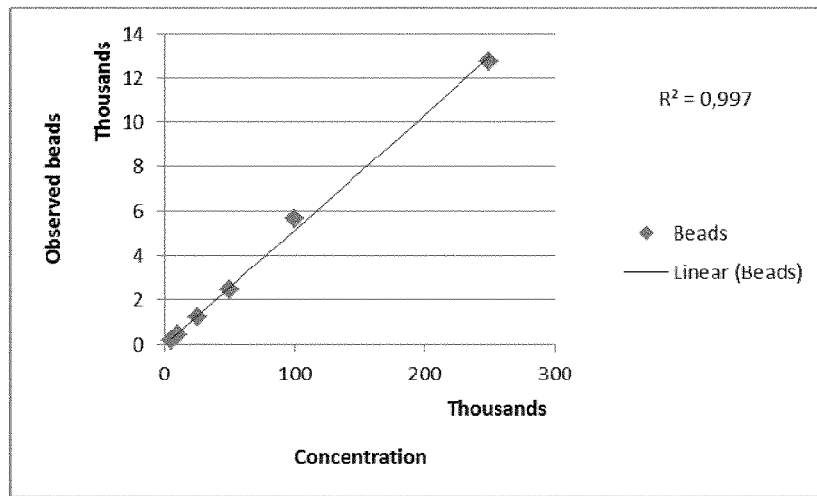
FIG. 6 illustrates a correlation graph showing the nearly perfect relation between the number of beads observed (Y axis) from sample tubes and the known concentration ranging from to 250 000, beads (x-axis).
Figure 7:
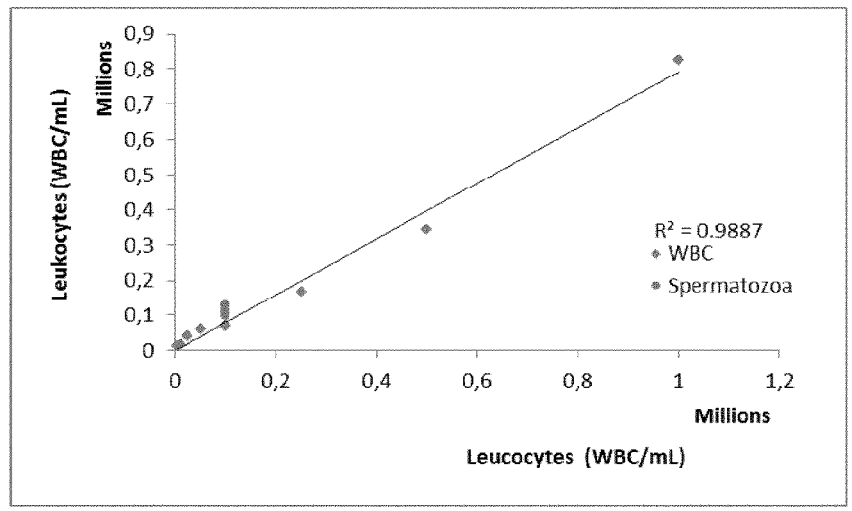
FIG. 7 illustrates a correlation graph showing leukocyte concentration determined (Y axis) from sample tubes known to contain 5000, 10 000, 25 000, 50 000, 100 000, 250 000, 500 000 and 1M leukocytes (x-axis).
Figure 8:
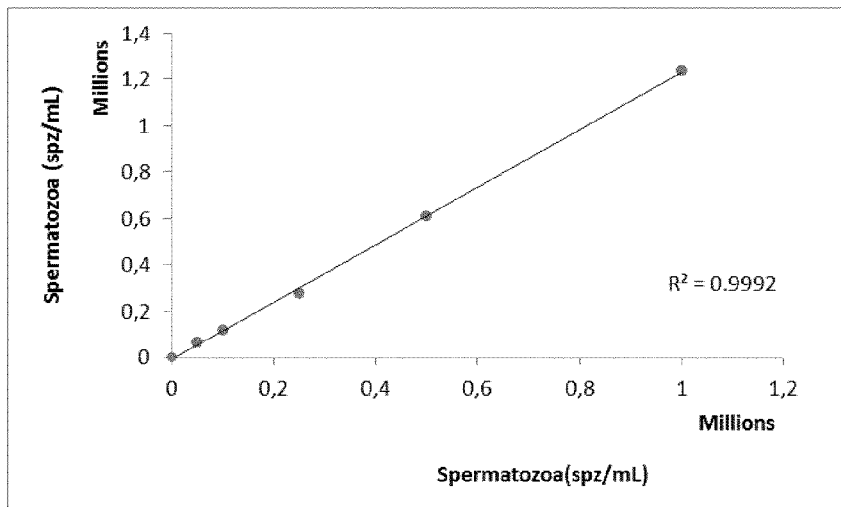
FIG. 8 illustrates a correlation graph showing spermatozoa concentration determined (Y axis) from sample tubes known to contain 20 000, 40 000, 70 000, 100 000, 250 000, 500 000 and 1M spermatozoa (x-axis).

Spermatozoa and leukocyte concentrations were determined by mathematical comparison against the number of beads analyzed. FIGS. 6, 7 and 8 demonstrate the linearity in determining proper concentration of the cells (Pearson coefficients ≥0.99).

Example 3

A volume of semen equivalent to a concentration of 500 000 spermatozoa was added to a cytometry tube containing 1 µL of anti-human CD46 coupled to FITC (AbD Serotec MCA2113FT) and enough HTF media to complete the volume to 473 µl. The tube was incubated at 37° C. for 15 minutes. Then 5 µl of anti-human CD45 was added to the tube. Incubation was then prolonged for an additional 5 minutes. Then 1 µl of 5 mg/mL Dapi (Molecular Probes D3571) was added to the tube. The incubation was then prolonged again for an additional 10 minutes for a total of 30 minutes of incubation. Then twenty five thousand (25 000) beads (21 µl of beads suspension) were added for the determination of leukocyte concentration for a final volume of 500 µl.

This analysis allows for simultaneous determination of spermatozoa viability, spermatozoa acrosomal integrity and leukocyte concentration. This analysis also avoid detecting leukocyte viability as spermatozoa viability or the opposite or artefacts in the acrosomal integrity measurements that could be caused by intervening cells like leukocytes.

Gate 1 was created by displaying all events on a forward scatter vs. side scatter density plot and by selecting the population of spermatozoa.

Gate 2 was created by displaying gate 1 on a CD45 intensity frequency histogram and by selecting spermatozoa as anti-CD45 negatives.

Gate 3 was created by displaying all events forward scatter vs. side scatter density plot and by selecting the population of beads.

Gate 4 was created by displaying gate 3 on a Dapi intensity frequency histogram and by selecting the main population as beads.

Gate 5 was created by displaying all events on a side-scatter vs. forward scatter density plot and by selecting the populations that corresponds to leukocytes.

Gate 6 was created by displaying gate 5 events on a CD45 fluorescence intensity frequency histogram and by selecting the CD45 positive population as the leukocytes.

Spermatozoa and leukocytes number and concentration were determined by mathematical comparison with the number of beads evaluated.

Gate 7 was created by displaying gate 2 on a dapi fluorescence intensity frequency histogram and by selecting the negative population as living spermatozoa.

The reference value of normal leukocyte concentration in semen is 1 million/mL. In the case of fertility spermograms, leukocyte concentration is difficult to determine as well for the same reason of low concentration.

The method presented herein can be used to enumerate leukocytes precisely and quantitatively within a semen sample.

The reference value for sperm viability is 58%.

Acrosomal reaction of the living cells is determined by displaying gate 2 on a DAPI vs. CD46 density plot and by selecting the Dapi negative/CD46 positive cells.

Total acrosomal loss is determined by selecting all PNA positive cells. Acrosomal reaction of the living cells should be lower than 12% and total acrosomal loss should be lower than 40% (International Braz J. Urol Vol. 33 (3): 364-376, May-June, 2007).

Other types of analysis can be done for fertility assessment or post-vasovasostomy. Typically, the fertility spermogram is performed as per WHO's manual recommendations. But here, in addition to the standard procedures, the equivalent of 500 000 spermatozoa are incubated into a tube already containing DAPI for spermatozoa viability assessment, peanut agglutinin for acrosomal integrity and a PerCp-conjugated anti-human CD45 antibody for leukocyte identification. The volume is completed with Irvine Human Tubal Fluid (HTF).

It is understood that the data reported in the present specification are only given to illustrate the invention and may not be regarded as constituting a limitation thereof.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All published documents mentioned in the above specification are herein incorporated by reference.

The invention claimed is:

1. A method for determining the amount of spermatozoa in a post-vasectomy semen sample obtained from a human subject, the method comprising:
    a) contacting the post-vasectomy semen sample with: i) a DNA dye; and ii) a leukocyte-specific detection agent; and
    b) subjecting the post-vasectomy semen sample of step a) to flow cytometry to distinguish the spermatozoa from leukocytes based on measurement of the DNA dye and on measurement of the leukocyte-specific detection agent; and
    wherein the amount of spermatozoa identified in b) is indicative of the amount of spermatozoa in the post-vasectomy semen sample.

2. The method as defined in claim 1, wherein the leukocyte-specific detection agent is a leukocyte-specific antibody.

3. The method as defined in claim 2, wherein the leukocyte-specific antibody is directed against CD45.

4. The method as defined in claim 1, wherein step a) further comprises contacting the post-vasectomy semen sample with: iii) a cell viability dye.

5. The method as defined in claim 4, wherein the cell viability dye is 3,3'-dihexyloxacarbocyanine iodide (DiOC6).

6. The method as defined in claim 1, wherein the DNA dye is selected from a Hoechst dye, DAPI, and propidium iodide.

7. The method as defined in claim 6, wherein the DNA dye is a Hoechst dye.

8. The method as defined in claim 1, wherein the leukocyte-specific detection agent is selected from antibodies against CD44, CD45, CD47R, CD50, CD53, CD54, CD55, CD58 and CD59.

9. The method as defined in claim 1, wherein step a) further comprises contacting the post-vasectomy semen sample with: iii) standardization particles.

10. The method as defined in claim 9, wherein step b) further comprises using side and forward light scattering and selecting for the spermatozoa.

11. The method as defined in claim 9, wherein step b) further comprises using side and forward light scattering and selecting for the standardization particles.

12. The method as defined in claim 9, wherein step b) further comprises using side and forward light scattering and selecting for the leukocytes.

13. A method for determining the amount of spermatozoa in an oligozoospermic semen sample obtained from a human subject, the method comprising:
    a) obtaining a diluted semen sample from the oligozoospermic semen sample;
    b) simultaneously contacting the diluted semen sample of step a) with: i) a DNA dye, and ii) a leukocyte-specific detection agent, and iii) standardization particles; and
    c) subjecting the diluted semen sample of step b) to flow cytometry to distinguish the spermatozoa from leukocytes and from the standardization particles based on measurement of the DNA dye and on measurement of the leukocyte-specific detection agent and on the measurement of the standardization particles; and
wherein the amount of spermatozoa identified in the diluted sample of c) is indicative of the amount of spermatozoa in the oligozoospermic semen sample.

14. The method as defined in claim 13, wherein step b) further comprises simultaneously contacting the oligozoospermic semen sample with: iv) a cell viability dye.

15. The method as defined in claim 13, wherein the DNA dye is a Hoechst dye and the leukocyte-specific detection agent is an antibody against CD45.

* * * * *